United States Patent
Rezaee

(10) Patent No.: US 9,626,476 B2
(45) Date of Patent: Apr. 18, 2017

(54) APPARATUS, METHOD AND COMPUTER-READABLE STORAGE MEDIUM FOR TRANSFORMING DIGITAL IMAGES

(71) Applicant: McKesson Financial Holdings, Hamilton (BM)

(72) Inventor: Mahmoud Ramze Rezaee, North Vancouver (CA)

(73) Assignee: Change Healthcare LLC, San Francisco, CA (US)

( * ) Notice: Subject to any disclaimer, the term of this patent is extended or adjusted under 35 U.S.C. 154(b) by 37 days.

(21) Appl. No.: 14/227,382

(22) Filed: Mar. 27, 2014

(65) Prior Publication Data

US 2015/0278442 A1  Oct. 1, 2015

(51) Int. Cl.
*G06K 9/00* (2006.01)
*G06F 19/00* (2011.01)

(52) U.S. Cl.
CPC .................................. *G06F 19/321* (2013.01)

(58) Field of Classification Search
None
See application file for complete search history.

(56) References Cited

U.S. PATENT DOCUMENTS

| | | |
|---|---|---|
| 4,340,911 A | 7/1982 | Kato et al. |
| 4,945,478 A | 7/1990 | Merickel et al. |
| 5,133,020 A | 7/1992 | Giger et al. |
| 5,452,367 A | 9/1995 | Bick et al. |
| 5,454,050 A | 9/1995 | Nakabayashi et al. |
| 5,579,360 A | 11/1996 | Abdel-Mottaleb |
| 5,757,953 A | 5/1998 | Jang |
| 5,790,690 A | 8/1998 | Doi et al. |
| 5,809,161 A | 9/1998 | Auty et al. |
| 5,818,624 A | 10/1998 | Patterson et al. |

(Continued)

OTHER PUBLICATIONS

Adams, R., et al.; "Seeded region growing"; IEEE Transactions on Pattern Anayisis and Machine Intelligence; vol. 16; Issue 6; Jun. 1994; pp. 641-647.

(Continued)

*Primary Examiner* — Abita O Fitzpatrick
(74) *Attorney, Agent, or Firm* — Alston & Bird LLP

(57) ABSTRACT

An apparatus, method and computer-readable storage medium are provided for processing images, such as medical images, in accordance with an imaging calibration function during execution of an image viewing application, and also for processing other types of images with a different calibration function during execution of a different application. In regards to an apparatus, the apparatus is caused to identify, in conjunction with an image viewing application, an imaging calibration function. The apparatus is also caused to transform a digital image during execution of the image viewing application in accordance with the imaging calibration function and to output the digital image, following transformation, in accordance with the image viewing application. In conjunction with a different application, the apparatus is caused to identify a second calibration function, different than the imaging calibration function, and to cause output of a digital image following transformation in accordance with the second calibration function.

20 Claims, 7 Drawing Sheets

(56) References Cited

U.S. PATENT DOCUMENTS

| | | |
|---|---|---|
| 5,832,103 A | 11/1998 | Giger et al. |
| 5,832,118 A | 11/1998 | Kim |
| 6,072,892 A | 6/2000 | Kim |
| 6,091,841 A | 7/2000 | Rogers et al. |
| 6,282,307 B1 | 8/2001 | Armato, III et al. |
| 6,463,173 B1 | 10/2002 | Tretter |
| 6,546,130 B1 | 4/2003 | Inoue et al. |
| 6,865,297 B2 | 3/2005 | Loui et al. |
| 6,985,612 B2 | 1/2006 | Hahn |
| 7,136,518 B2 | 11/2006 | Griffin et al. |
| 7,324,669 B2 | 1/2008 | Nakanishi et al. |
| 7,391,895 B2 | 6/2008 | Wang et al. |
| 7,459,696 B2 | 12/2008 | Schomacker et al. |
| 7,469,160 B2 | 12/2008 | Banks et al. |
| 7,756,316 B2 | 7/2010 | Odry et al. |
| 7,822,255 B2 | 10/2010 | Schutz |
| 7,903,861 B2 | 3/2011 | Luo et al. |
| 8,260,048 B2 | 9/2012 | Jin |
| 2002/0028008 A1 | 3/2002 | Fan et al. |
| 2002/0165837 A1 | 11/2002 | Zhang et al. |
| 2003/0169915 A1 | 9/2003 | Takeo |
| 2003/0212327 A1 | 11/2003 | Wang et al. |
| 2004/0008886 A1 | 1/2004 | Boykov |
| 2004/0196250 A1 | 10/2004 | Mehrotra et al. |
| 2004/0258305 A1 | 12/2004 | Burnham et al. |
| 2005/0174309 A1 | 8/2005 | Bouwens et al. |
| 2006/0159321 A1 | 7/2006 | Takeo et al. |
| 2007/0014488 A1 | 1/2007 | Chen et al. |
| 2007/0055143 A1* | 3/2007 | Deroo et al. ............ 600/425 |
| 2007/0086640 A1 | 4/2007 | Luo et al. |
| 2007/0120763 A1* | 5/2007 | De Paepe ............ G06F 3/03547 345/1.3 |
| 2008/0002872 A1 | 1/2008 | Gatesoupe et al. |
| 2008/0089568 A1 | 4/2008 | Delenstarr |
| 2008/0094426 A1 | 4/2008 | Kimpe |
| 2008/0123918 A1* | 5/2008 | Saotome ............... G06T 5/009 382/128 |
| 2008/0130964 A1 | 6/2008 | Zwirn et al. |
| 2008/0212864 A1 | 9/2008 | Bornefalk |
| 2008/0266413 A1 | 10/2008 | Cohen et al. |
| 2009/0003672 A1 | 1/2009 | Maier et al. |
| 2009/0129673 A1 | 5/2009 | Simon et al. |
| 2009/0220139 A1 | 9/2009 | Schneider et al. |
| 2009/0232376 A1 | 9/2009 | Raundahl et al. |
| 2009/0324073 A1 | 12/2009 | Wengler et al. |
| 2010/0166281 A1 | 7/2010 | Burger et al. |
| 2010/0272367 A1 | 10/2010 | Criminisi et al. |
| 2010/0322489 A1 | 12/2010 | Tizhoosh et al. |
| 2011/0013819 A1 | 1/2011 | Raundahl et al. |
| 2011/0158491 A1 | 6/2011 | Markova et al. |
| 2011/0182501 A1 | 7/2011 | Mercier et al. |
| 2011/0257519 A1 | 10/2011 | Bjornerud et al. |
| 2012/0014585 A1 | 1/2012 | Morita et al. |
| 2012/0093399 A1 | 4/2012 | Paik et al. |
| 2012/0207366 A1 | 8/2012 | Liu |
| 2012/0229490 A1* | 9/2012 | Rezaee ............... G09G 5/10 345/589 |
| 2013/0016884 A1 | 1/2013 | El-Hilo et al. |
| 2013/0187958 A1 | 7/2013 | Kimpe et al. |
| 2013/0287313 A1 | 10/2013 | Marchessoux et al. |

OTHER PUBLICATIONS

Arifin, A.Z., et al.; "Image segmentation by histogram thresholding using hierarchical cluster analysis"; Pattern Recognition Letters; 2006; pp. 1-7.

Besl, P.J., et al.; "Segmentation Through Variable-Order Surface Fitting"; IEEE Transactions on Pattern Analysis and Machine Intelligence; vol. 10; Issue 2; Mar. 1998; pp. 167-192.

Cootes, T.F., et al.; "Active Appearance Models"; IEEE Transactions on Pattern Analysis and Machine Intelligence; vol. 23; No. 6; Jun. 2001; pp. 681-685.

Cootes, T.F., et al.; "Active Shape Models—Their Training and Application"; Computer Vision and Image Understanding; vol. 61; Issue 1; Jan. 1995; pp. 38-59.

Dijkstra, E.W.; "A Note on Two Problems in Connexion with Graphs"; Numerische Mathematik; vol. 1; 1959; pp. 269-271.

Pham, D.L., et al.; "Current Methods in Medical Image Segmentation"; Annual Review of Biomedical Engineering; vol. 2; Aug. 2000; pp. 315-337.

Rezaee, M.R., et al.; "A Multiresolution Image Segmentation Technique Based on Pyramidal Segmentation and Fuzzy Clustering"; IEEE Transactions on Image Processing; vol. 9; Issue 7; Jul. 2000; pp. 1238-1248.

PS 3.14-2009, Digital Imaging and Communications in Medicine (DICOM), Part 14: Grayscale Standard Display Function; National Electrical Manufacturers Association, 2009; 55 pages.

Tanaka, et al.; Application of Grayscale Standard Display Funtion to General Purpose Liquid-Crystal Display Monitors for Clinical Use; pp. 25-32.

About Gamma Correction http://www.graphics.stanford.edu/gamma.html (3 pgs.) site visited Feb. 8, 2011 9:00 AM.

CGSD—Gamma Correction Explained http://www.siggraph.org/education/materials/HyperGraph/gamma_corr . . . (3 pgs.) Site visited Feb. 8, 2011 9:00 AM.

Notice of Allowance for U.S. Appl. No. 13/233,656 dated Jan. 7, 2013.

Office Action for U.S. Appl. No. 13/182,055; dated Aug. 16, 2013.

Notice of Allowance for U.S. Appl. No. 13/182,055 dated Mar. 11, 2014.

Notice of Allowance for U.S. Appl. No. 13/182,055 dated May 5, 2014.

Notice of Allowance for U.S. Appl. No. 13/044,122 dated Aug. 25, 2014.

Notice of Allowance for U.S. Appl. No. 14/317,353 dated Feb. 18, 2015.

Office Action for U.S. Appl. No. 13/044,122 dated Mar. 7, 2014.

Office Action for U.S. Appl. No. 14/317,353 dated Jul. 29, 2014.

* cited by examiner

APPARATUS, METHOD AND COMPUTER-READABLE STORAGE MEDIUM FOR TRANSFORMING DIGITAL IMAGES

TECHNOLOGICAL FIELD

Example embodiments of the present invention generally relate to the presentation of images and, more particularly, to the transformation of images to provide for enhanced viewing.

BACKGROUND

Medical imaging often includes creating images of the human body or parts of the human body for clinical purposes such as examination, diagnosis and/or treatment. These images may be acquired by a number of different imaging modalities including, for example, ultrasound (US), magnetic resonance (MR), positron emission tomography (PET), computed tomography (CT), mammograms (MG) digital radiology (DR), computed radiology (CR) or the like. In a number of example medical imaging workflows, an acquired image may be reviewed by a technician of the imaging modality, and then sent to a viewing station where the image may be reviewed by a medical professional such as a radiologist. This is the case, for example, in a Picture Archiving and Communication System (PACS).

Maintaining consistency in the quality of an acquired image through an imaging workflow is often desirable. Due to different monitor calibration functions between imaging modalities and viewing stations, however, an undesirable visualization discrepancy may occur. These calibration functions may be described as being performed by a modality or viewing station, but in more particular examples, may be performed by video drivers of the respective apparatuses, software associated with monitors of the respective apparatuses or the like. In one example, an imaging modality may apply a first calibration function such as the gamma correction function (e.g., $\gamma=2.2$) to an acquired image viewed by a monitor of the modality. The viewing station in this example, however, may apply a second, different calibration function to the acquired image viewed by a monitor of the viewing station—the second calibration function in one example being the DICOM GSDF. For more information on the DICOM GSDF, see National Electrical Manufacturers Association (NEMA), PS 3.14-2009, entitled: *Digital Imaging and Communications in Medicine (DICOM)—Part 14: Grayscale Standard Display Function*, the content of which is hereby incorporated by reference in its entirety.

In the above example, an imaging modality may have a particular gamma value (the value that describes the relationship between the varying levels of luminance that a monitor can display). This gamma value may differ from one imaging modality to another imaging modality, which may compound the undesirability of differences in monitor calibration functions in various instances in which a viewing station may receive images from different modalities.

Dedicated viewing stations were traditionally employed to view medical images. However, a wide range of computing devices may now be utilized to view medical images. In addition to dedicated viewing stations, such as those employed by PACS, a variety of computing devices, such as computer workstations, personal computers and mobile devices, such as laptop computers, tablet computers, mobile telephones, smartphones, personal digital assistants (PDAs) and the like, may be utilized to view medical images.

Although users have become accustomed to viewing medical images that have been calibrated in accordance with DICOM GSDF, some computing devices, such as mobile devices, that may be utilized to view medical images may not be configured to calibrate medical images in accordance with DICOM GSDF. Instead, the computing devices, such as mobile devices, may be configured to calibrate images in accordance with another type of calibration function, such as a calibration function designed for the display of video games, movies or other content. Thus, the images presented by these computing devices may not appear in the same manner as that with which users are accustomed and, as such, users may experience more difficulty in reading and interpreting the medical images.

BRIEF SUMMARY

In light of the foregoing background, example embodiments of the present invention provide an apparatus, method and computer-readable storage medium for transforming images, such as medical images, such that the image that is presented has an appearance with which the user is familiar and which may therefore be more readily read and interpreted. For example, the apparatus, method and computer-readable storage medium of an example embodiment may process images in a manner that causes images to appear to have been presented upon a device that has been calibrated in accordance with DICOM GSDF. Additionally, the apparatus, method and computer-readable storage medium of an example embodiment may permit transformation in accordance with an imaging calibration function during execution of an image viewing application, but in accordance with a different calibration function during execution of a different application, thereby supporting the presentation of images by computing devices that are not necessarily dedicated to viewing medical images.

According to an example embodiment, an apparatus is provided that includes a processor and a memory storing executable instructions that in response to execution by the processor cause the apparatus to at least perform a number of operations. In this regard, the apparatus is caused to identify, in conjunction with an image viewing application, an imaging calibration function. The apparatus of this example embodiment is also caused to transform a digital image during execution of the image viewing application that includes a plurality of pixels each of which has a pixel value of a plurality of pixel values. In this regard, the digital image may be transformed by transforming the pixel value of at least some of the pixels to corresponding transformed pixel values processed according to the imaging calibration function. In this example embodiment, the apparatus is also caused to cause output of the digital image in accordance with the image viewing application. In this regard, the digital image that is output includes the plurality of pixels of which at least some have a transformed pixel value. In conjunction with a second application, different than the image viewing application, the apparatus of this example embodiment is caused to identify a second calibration function, different than the imaging calibration function. Further, the apparatus of this example embodiment is caused to cause output of a digital image in accordance with the second application. In this regard, the digital image that is output includes a plurality of pixels of which at least some have been transformed in accordance with the second calibration function.

The apparatus may be caused to transform the digital image during execution of the image viewing application by being caused to transform the pixel value according to a lookup table associated with the imaging calibration function. In this example embodiment, the apparatus may be further caused, during execution of the second application, to transform the digital image by transforming the pixel value of at least some of the pixels to corresponding transformed pixel values processed according to the second calibration function. The apparatus of this example embodiment may also be caused to transform the digital image during execution of the second application by being caused to transform the pixel value according to a lookup table associated with the second calibration function. In this regard, the lookup table associated with the second calibration function is different than the lookup table associated with the imaging calibration function.

The apparatus may be caused to output the digital image by being caused to present the digital image upon a display. In this regard, the imaging calibration function is dependent upon a type of the display. In this example embodiment, the apparatus is further caused to determine the type of display upon which the digital image is to be presented and to identify the imaging calibration function by identifying the imaging calibration function based upon the type of display. In this example embodiment, the memory may be configured to store a plurality of imaging calibration functions with each imaging calibration function associated with a respective type of display.

The apparatus may be further caused to set the imaging calibration function as an active calibration function upon actuation of the image viewing application and identification of the imaging calibration function and to reset the second calibration function as the active calibration function once the image viewing application is exited. In this example embodiment, the apparatus is caused to transform the digital image by being caused to transform the digital image in accordance with the active calibration function.

According to another example embodiment, a method is provided that includes identifying, in conjunction with an image viewing application, an imaging calibration function. The method of this example embodiment also includes transforming a digital image during execution of the image viewing application that includes a plurality of pixels each of which has a pixel value of a plurality of pixel values. In this regard, the digital image may be transformed by transforming the pixel value of at least some of the pixels to corresponding transformed pixel values processed according to the imaging calibration function. In this example embodiment, the method also includes causing output of the digital image in accordance with the image viewing application. In this regard, the digital image that is output includes the plurality of pixels of which at least some have a transformed pixel value. In conjunction with a second application, different than the image viewing application, the method of this example embodiment includes identifying a second calibration function, different than the imaging calibration function. Further, the method of this example embodiment includes causing output of a digital image in accordance with the second application. In this regard, the digital image that is output includes a plurality of pixels of which at least some have been transformed in accordance with the second calibration function.

The method may transform the digital image during execution of the image viewing application by transforming the pixel value according to a lookup table associated with the imaging calibration function. In this example embodiment, the method may, during execution of the second application, transform the digital image by transforming the pixel value of at least some of the pixels to corresponding transformed pixel values processed according to the second calibration function. The method of this example embodiment may also transform the digital image during execution of the second application by transforming the pixel value according to a lookup table associated with the second calibration function. In this regard, the lookup table associated with the second calibration function is different than the lookup table associated with the imaging calibration function.

The method may cause the digital image to be output by causing the digital image to be presented upon a display. In this regard, the imaging calibration function is dependent upon a type of the display. In this example embodiment, the method also includes determining the type of display upon which the digital image is to be presented and identifying the imaging calibration function by identifying the imaging calibration function based upon the type of display. In this example embodiment, the method may also include storing a plurality of imaging calibration functions with each imaging calibration function associated with a respective type of display.

The method may also include setting the imaging calibration function as an active calibration function upon actuation of the image viewing application and identification of the imaging calibration function and resetting the second calibration function as the active calibration function once the image viewing application is exited. In this example embodiment, the method transforms the digital image by transforming the digital image in accordance with the active calibration function.

According to a further example embodiment, a non-transitory computer-readable storage medium is provided that has computer-readable program code portions stored therein that, in response to execution by a processor, cause an apparatus to at least perform a number of operations. In this regard, the apparatus is caused to identify, in conjunction with an image viewing application, an imaging calibration function. The apparatus of this example embodiment is also caused to transform a digital image during execution of the image viewing application that includes a plurality of pixels each of which has a pixel value of a plurality of pixel values. In this regard, the digital image may be transformed by transforming the pixel value of at least some of the pixels to corresponding transformed pixel values processed according to the imaging calibration function. In this example embodiment, the apparatus is also caused to cause output of the digital image in accordance with the image viewing application. In this regard, the digital image that is output includes the plurality of pixels of which at least some have a transformed pixel value. In conjunction with a second application, different than the image viewing application, the apparatus of this example embodiment is caused to identify a second calibration function, different than the imaging calibration function. Further, the apparatus of this example embodiment is caused to cause output of a digital image in accordance with the second application. In this regard, the digital image that is output includes a plurality of pixels of which at least some have been transformed in accordance with the second calibration function.

The apparatus may be caused by execution of the computer-readable program code portions to transform the digital image during execution of the image viewing application by being caused to transform the pixel value according to a lookup table associated with the imaging calibration function. In this example embodiment, the apparatus may be further caused, during execution of the second application, to transform the digital image by transforming the pixel value of at least some of the pixels to corresponding transformed pixel values processed according to the second calibration function. The apparatus of this example embodiment may also be caused to transform the digital image during execution of the second application by being caused to transform the pixel value according to a lookup table associated with the second calibration function. In this regard, the lookup table associated with the second calibration function is different than the lookup table associated with the imaging calibration function.

The apparatus may be caused by execution of the computer-readable program code portions to output the digital image by being caused to present the digital image upon a display. In this regard, the imaging calibration function is dependent upon a type of the display. In this example embodiment, the apparatus is further caused to determine the type of display upon which the digital image is to be presented and to identify the imaging calibration function by identifying the imaging calibration function based upon the type of display.

The apparatus may be further caused by execution of the computer-readable program code portions to set the imaging calibration function as an active calibration function upon actuation of the image viewing application and identification of the imaging calibration function and to reset the second calibration function as the active calibration function once the image viewing application is exited. In this example embodiment, the apparatus is caused to transform the digital image by being caused to transform the digital image in accordance with the active calibration function.

BRIEF DESCRIPTION OF THE DRAWINGS

Figure 1:
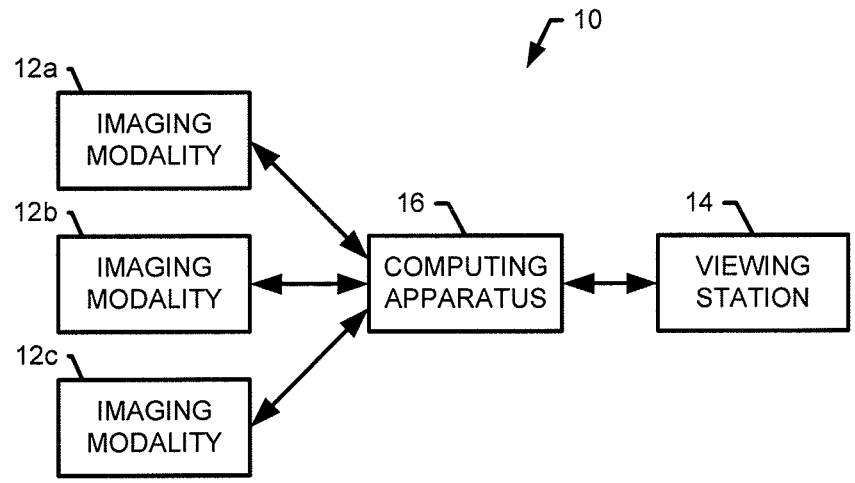
Figure 2:
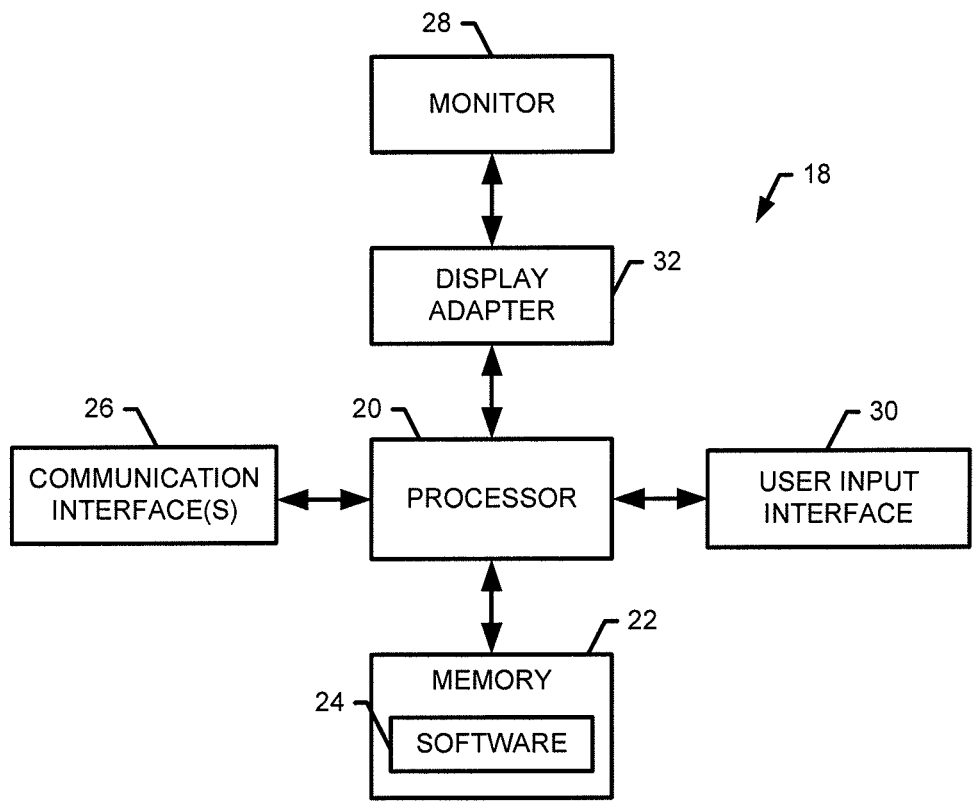
Figure 3:
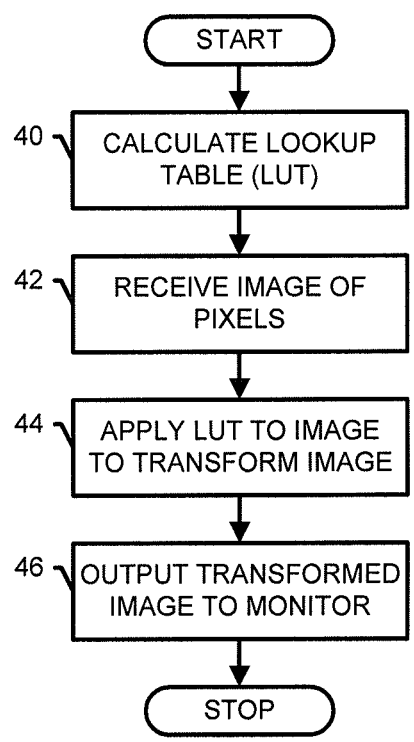
Figure 4:
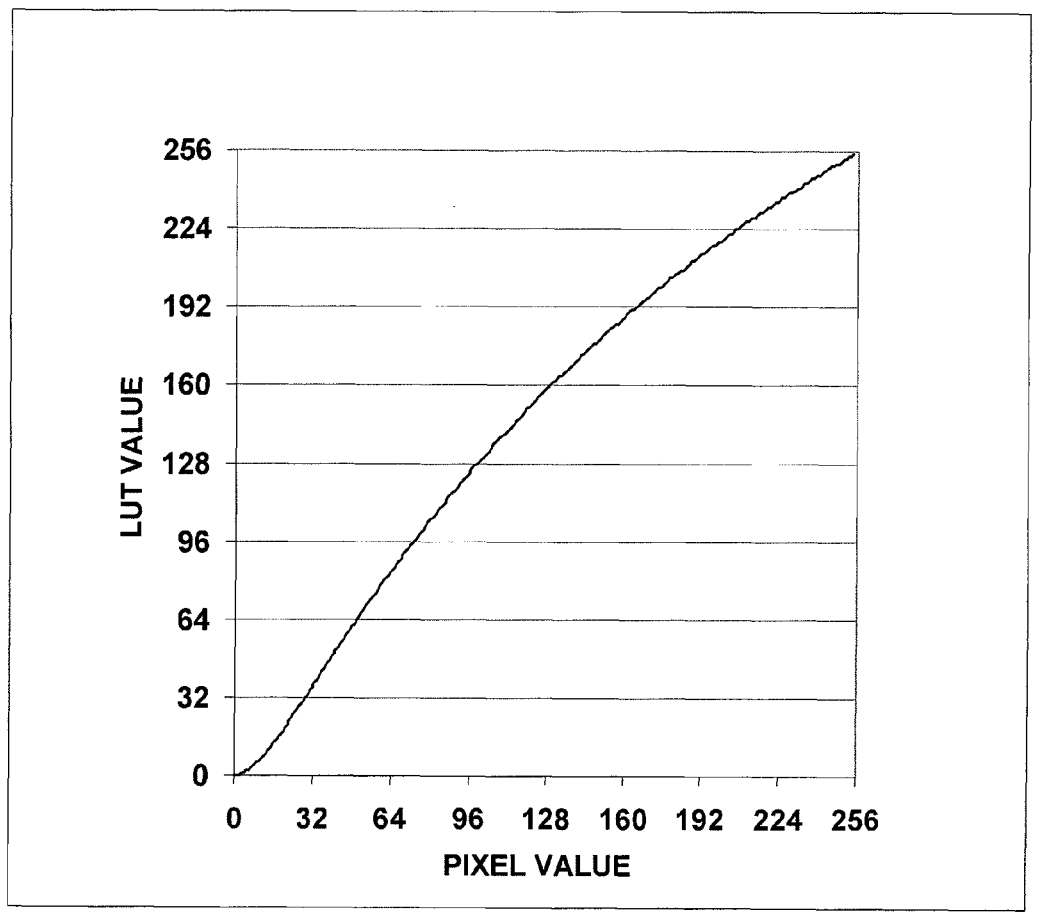
Figure 5:
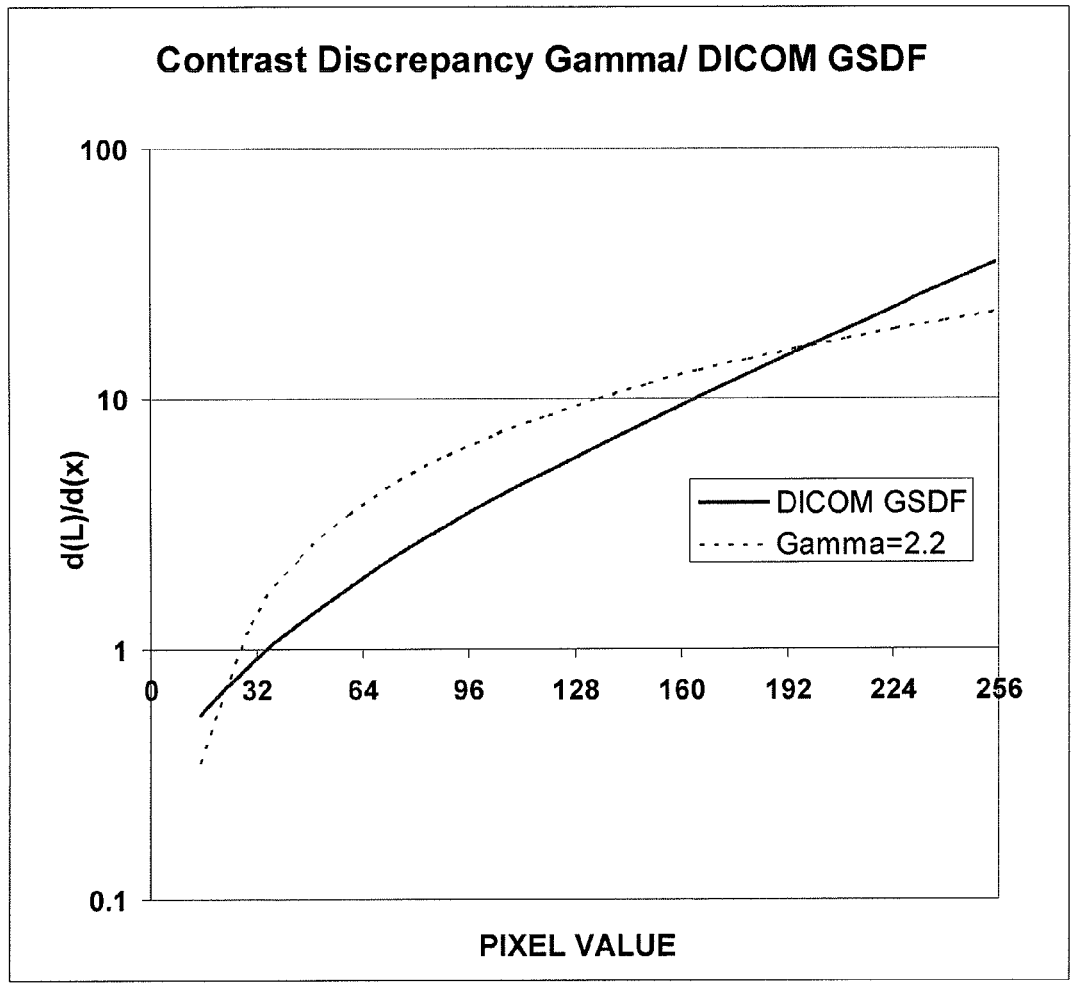
Figure 6:
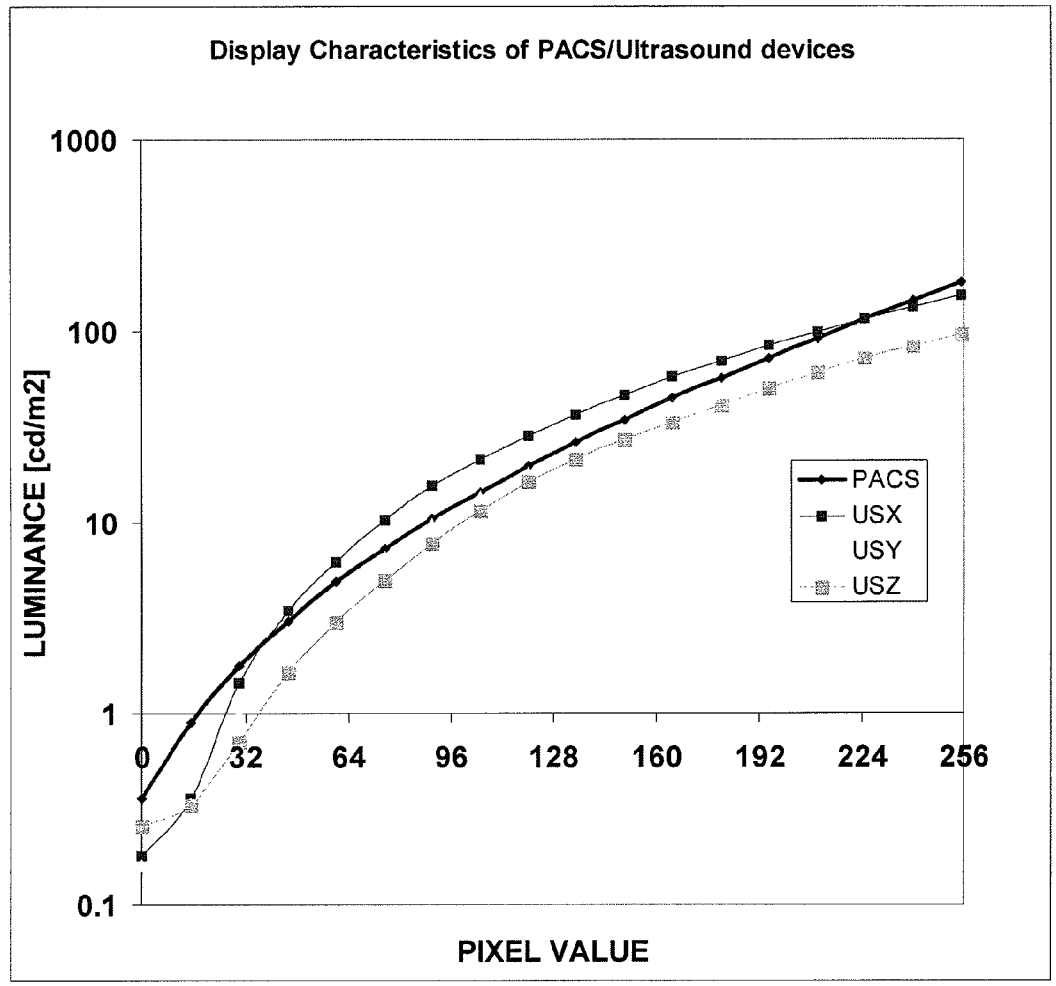
Figure 7:
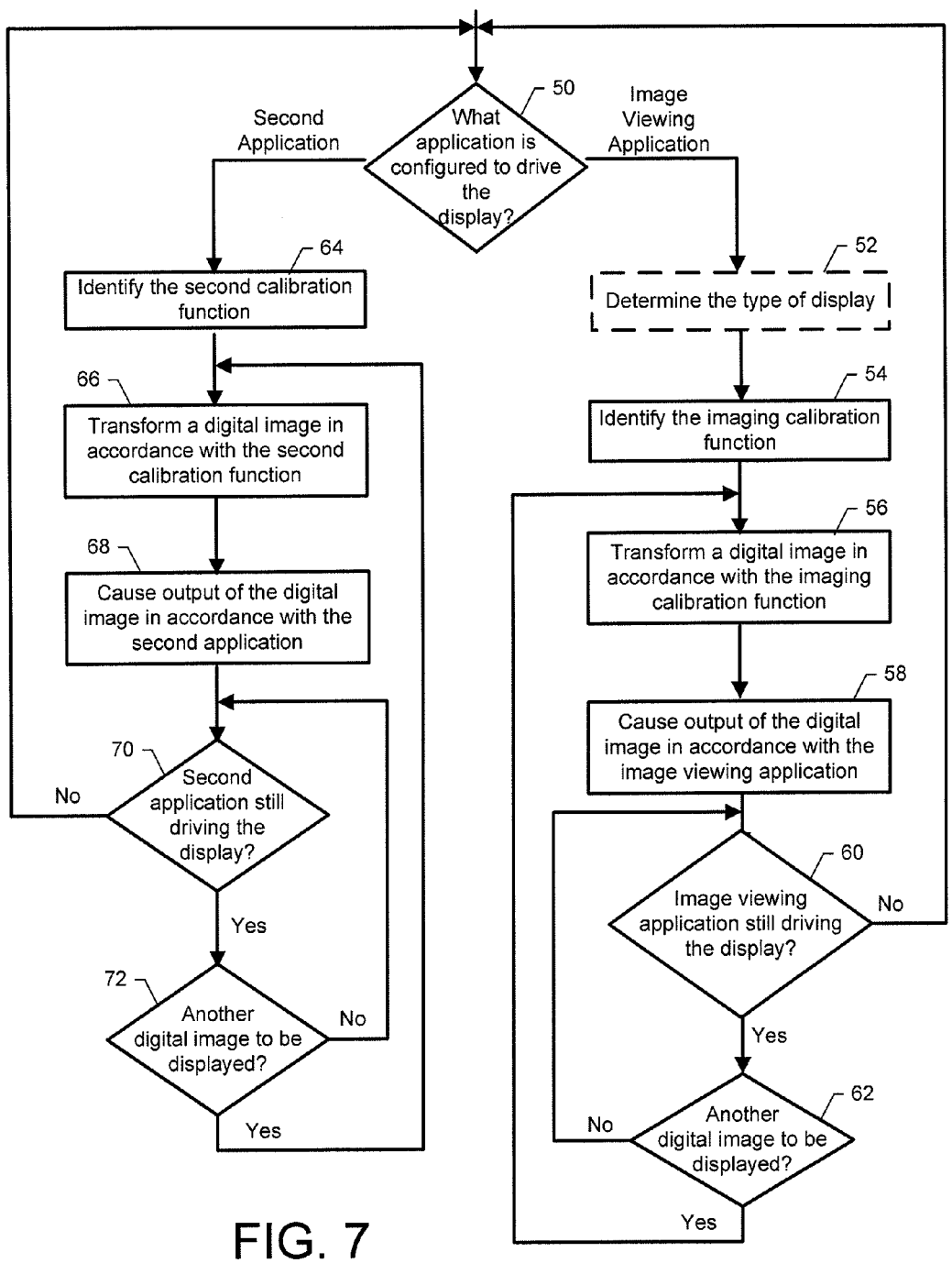
Figure 8:
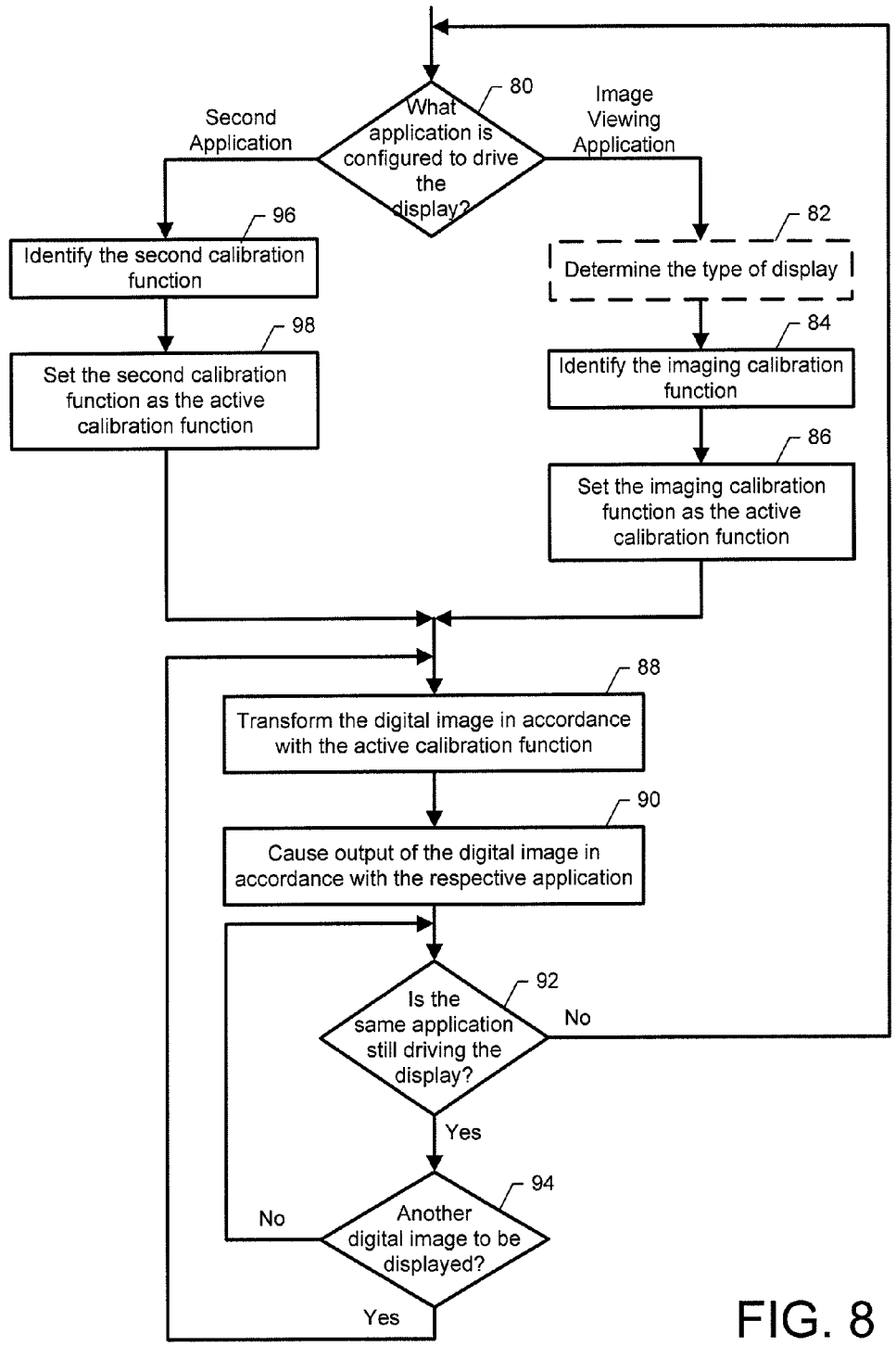

Having thus described example embodiments of the invention in general terms, reference will now be made to the accompanying drawings, which are not necessarily drawn to scale, and wherein:

FIG. 1 is a schematic block diagram of a system configured to operate in accordance with an example embodiments of the present invention;

FIG. 2 is a schematic block diagram of an apparatus that may be configured to operate as or otherwise perform one or more functions of one or more of the components of the system of FIG. 1, in accordance with embodiments of the present invention; and FIG. 3 is a flowchart illustrating various operations in a method according to an example embodiment of the present invention;

FIG. 4 is a graph that illustrates lookup table (LUT) values for an example image, according to one example embodiment of the present invention;

FIG. 5 is a graph that illustrates a change in image contrast due to different calibration functions, according to example embodiments of the present invention;

FIG. 6 is a graph that illustrates display characteristics of a PACS monitor and three ultrasound devices, according to one example embodiment of the present invention;

FIG. 7 is a flowchart illustrating operations performed, such as by the apparatus of FIG. 2, in accordance with an example embodiment of the present invention; and FIG. 8 is a flowchart illustrating operations performed, such as by the apparatus of FIG. 2, in accordance with another example embodiment of the present invention.

DETAILED DESCRIPTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Further, the apparatus and method of example embodiments of the present invention will be primarily described in conjunction with medical-imaging applications. It should be understood, however, that the apparatus and method can be utilized in conjunction with a variety of other applications, both in the medical industry and outside of the medical industry. Like numbers refer to like elements throughout.

FIG. 1 illustrates a system 10 that may benefit from an example embodiment of the present invention. As shown, the system includes one or more imaging modalities 12 (three example modalities being shown as modalities 12a, 12b and 12c, although the system may include any number of modalities including a single modality) for acquiring an image, such as an image of the human body or parts of the human body for clinical purposes such as examination, diagnosis and/or treatment. Examples of suitable modalities include, for example, ultrasound (US), magnetic resonance (MR), positron emission tomography (PET), computed tomography (CT), mammograms (MG) digital radiology (DR), computed radiology (CR) or the like.

The system also includes a viewing station 14 configured to receive an image from one or more modalities 12, and present the image such as for review by a user, such as a medical professional, e.g., a radiologist. Although the viewing station may be a Picture Archiving and Communication System (PACS) viewing station (or workstation), the viewing station may be provided by the display of a computing device, such as a computer workstation, a desktop computer, a personal computer, a server, a mobile device, such as a laptop computer, a tablet computer, a mobile telephone, a smartphone, a personal digital assistant (PDA) and the like. As the foregoing examples illustrate, the computing device that is configured to present the images for review need not be dedicated to the presentation of medical images, but may execute a wide variety of applications, at least some of which may require the images to be transformed in different manners.

As explained in the background section, in various instances, a modality 12 and viewing station 14 may apply different monitor calibration functions to images presented by monitors of the respective apparatuses. For example, a modality may apply the gamma correction function, while the viewing station may apply a different calibration function. This difference in monitor calibration functions may lead to an undesirable visual discrepancy between an image presented by the modality, and the same image presented by the viewing station. As explained in greater detail below, the system of an example embodiment of the present invention may therefore further include a computing apparatus 16 configured to transform pixel values calibrated according to a first calibration function (e.g., gamma correction) to corresponding pixel values calibrated according to a second, different calibration function. In this manner, the computing apparatus of an example embodiment may compensate for visual discrepancies otherwise due to the different calibration functions.

The imaging modality 12, viewing station 14 and/or computing apparatus 16 may be configured to directly and/or indirectly communicate with one another in any of a number of different manners including, for example, any of a number of wireline or wireless communication or networking techniques. Examples of such techniques include, without limitation, Universal Serial Bus (USB), radio frequency (RF), Bluetooth (BT), infrared (IrDA), any of a number of different cellular (wireless) communication techniques such as any of a number of 2G, 2.5G or 3G communication techniques, local area network (LAN), wireless LAN (WLAN) techniques or the like. In accordance with various ones of these techniques, the imaging modality, viewing station 14 and/or computing apparatus can be coupled to and configured to communicate across one or more networks. The network(s) can comprise any of a number of different combinations of one or more different types of networks, including data and/or voice networks. For example, the network(s) can include one or more data networks, such as a LAN, a metropolitan area network (MAN), and/or a wide area network (WAN) (e.g., Internet), and include one or more voice networks, such as a public-switched telephone network (PSTN). Although not shown, the network(s) may include one or more apparatuses such as one or more routers, switches or the like for relaying data, information or the like between the imaging modality, viewing station and/or computing apparatus. In one embodiment, the viewing station 14 and the computing apparatus 16 may be embodied by the same computing device.

Reference is now made to FIG. 2, which illustrates a block diagram of an apparatus 18 that may be configured to operate as or otherwise perform one or more functions of an imaging modality 12, viewing station 14 and/or computing apparatus 16. The apparatus 18 may be embodied by or otherwise associated with the computing device. As such, in the example embodiment in which the viewing station 14 and the computing apparatus 16 are embodied by the same computing device, the apparatus may corresponding embody or otherwise be associated with both the viewing station and the computing apparatus.

The apparatus of an example embodiment of the present invention includes various means for performing one or more functions in accordance with example embodiments of the present invention, including those more particularly shown and described herein. It should be understood, however, that one or more of the entities may include alternative means for performing one or more like functions, without departing from the spirit and scope of the present invention.

As shown in FIG. 2, the apparatus may include a processor 20 connected to a memory 22. The memory can comprise volatile and/or non-volatile memory, and typically stores content, data or the like. In this regard, the memory may store one or more software applications 24, modules, instructions or the like for the processor to perform steps associated with operation of the apparatus in accordance with embodiments of the present invention. The memory may also store content transmitted from, and/or received by, the apparatus. As described herein, the software application(s) may each comprise software operated by the apparatus. It should be understood, however, that any one or more of the software applications described herein may alternatively be implemented by firmware, hardware or any combination of software, firmware and/or hardware, without departing from the spirit and scope of the present invention.

In addition to the memory 22, the processor 20 can also be connected to at least one interface or other means for displaying, transmitting and/or receiving data, content or the like, such as in accordance with USB, RF, BT, IrDA, WLAN, LAN, MAN, WAN (e.g., Internet), PSTN techniques or the like. In this regard, the interface(s) can include at least one communication interface 26 or other means for transmitting and/or receiving data, content or the like. In addition to the communication interface(s), the interface(s) can also include at least one user interface that can include one or more earphones and/or speakers, a monitor 28, and/or a user input interface 30. The user input interface, in turn, can comprise any of a number of devices allowing the apparatus to receive data from a user, such as a microphone, a keypad, a touch-sensitive surface (integral or separate from the monitor), a joystick, or other input device. As will be appreciated, the processor may be directly connected to other components of the apparatus, or may be connected via suitable hardware. In one example, the processor may be connected to the monitor via a display adapter 32 configured to permit the processor to send graphical information to the monitor.

As indicated above, the system of an example embodiment of the present invention includes a computing apparatus 16 configured to transform pixel values calibrated according to a first calibration function (e.g., gamma correction) to corresponding pixel values calibrated according to a second, different calibration function. In this manner, the computing apparatus may compensate for visual discrepancies otherwise due to the different calibration functions. The computing apparatus may be configured to apply the transformation in any of a number of different manners. As explained below, the computing apparatus may be configured to transform pixel values using a lookup table (LUT). It should be understood, however, that the computing apparatus may be equally configured to transform pixel values using an algorithm such as that from which an appropriate LUT may be calculated.

Reference is now made to FIG. 3, which illustrates various operations of a method according to an example embodiment of the present invention. As shown in block 40, the method may include calculating or otherwise retrieving a LUT for transformation of pixel values calibrated according to a first calibration function (e.g., gamma correction) to corresponding pixel values calibrated according to a second, different calibration function—these corresponding pixel values at times being referred to as LUT values. More particularly, for example, consider pixel values calibrated according to a first calibration function. For each such pixel value, a corresponding LUT value calibrated according to a second calibration function may be determined by first determining the luminance for the pixel value calibrated according to the first calibration function, and then determining the pixel value calibrated according to the second calibration function that yields the determined luminance. The LUT may be calculated in a number of different manners, which may depend on whether the first and second calibration functions are known or unknown. Examples of calculating a LUT in each instance are presented below.

In an instance in which the first and second calibration functions are known, the LUT may be calculated based on the respective functions. In this instance, assume for example that the first calibration function (the function of the imaging modality 12) may be described by the following representation of modality luminance (ML), and that the second calibration function (the function of the viewing station 14) may be described by the following representation of the station luminance (SL):

$$ML = G(x) \tag{1}$$

$$SL = F(x) \tag{2}$$

In the preceding, x represents the pixel value that belongs to the domain $[-2^{n-1}, 2^{n-1}-1]$ for a signed image or $[0, 2^n-1]$ for an unsigned image (n representing the number of bits of the pixel value).

Given the above equations (1) and (2), the LUT of one example embodiment may be calculated in accordance with the following:

$$LUT = F^{-1}(G(x)) \quad (3)$$

where $F^{-1}$ denotes the inverse function of F. A solution for the above expression of the LUT exists in instances in which both functions F(x) and G(x) are monotone. This is the case, for example, for both gamma and DICOM GSDF functions. In addition, the SL range may be equal or larger than the ML range to thereby produce a unique solution, which may be the case with typical PACS monitors.

In a more particular example in which the first and second calibration functions are known, consider an instance in which the first calibration function is a gamma correction, and the second calibration function is the DICOM GSDF. In this example, the gamma function may be described as follows:

$$ML = G(x) = C \times x^\gamma + B \quad (4)$$

In equation (4), C and B represent the contrast and minimum luminance (brightness) of the monitor of the modality 12, which may be set by respective monitor controls. The variable x represents a normalized pixel value between 0 and 1, which may take into account minimum and the maximum pixel values, and $\gamma$ (gamma) represents the gamma value of the modality monitor. For a signed DICOM MONOCHROME2 image with pixel of range $[-2^{n-1}, 2^{n-1}-1]$, the corresponding ML range may be $(ML_{min}, ML_{max})$, where $ML_{min} = C \times (-2^{n-1})^\gamma + B$ and $ML_{max} = C \times (2^{n-1}-1)^\gamma + B$.

Also in this more particular example in which the second calibration function is the DICOM GSDF, the luminance of the monitor of the viewing station 14 may be derived from the following DICOM GSDF (a monotone function):

$$\log_{10} L(j) = \frac{a + c \cdot \text{Ln}(j) + e \cdot (\text{Ln}(j))^2 + g \cdot (\text{Ln}(j))^3 + m \cdot (\text{Ln}(j))^4}{1 + b \cdot \text{Ln}(j) + d \cdot (\text{Ln}(j))^2 + f \cdot (\text{Ln}(j))^3 + h \cdot (\text{Ln}(j))^4 + k \cdot (\text{Ln}(j))^5} \quad (5)$$

In the preceding, Ln refers to the natural logarithm, and j refers to an index (1 to 1023) of luminance levels of the just-noticeable differences (JND), where the JND may be considered the luminance difference of a given target under given viewing conditions that the average human observer can just perceive. In this regard, one step in the JND index j may result in a luminance difference that is a JND. Also in the preceding, the constants a-h, k and m may be set as follows: $a = -1.3011877$, $b = -2.5840191 \times 10^{-2}$, $c = 8.0242636 \times 10^{-2}$, $d = -1.0320229 \times 10^{-1}$, $e = 1.3646699 \times 10^{-1}$, $f = 2.8745620 \times 10^{-2}$, $g = -2.5468404 \times 10^{-2}$, $h = -3.1978977 \times 10^{-3}$, $k = 1.2992634 \times 10^{-4}$ and $m = 1.3635334 \times 10^{-3}$.

The inverse function of equation (5) is as follows:

$$j(L) = A + B \cdot \text{Log}_{10}(L) + C \cdot (\text{Log}_{10}(L))^2 + D \cdot (\text{Log}_{10}(L))^3 + E \cdot (\text{Log}_{10}(L))^4 + F \cdot (\text{Log}_{10}(L))^5 + G \cdot (\text{Log}_{10}(L))^6 + H \cdot (\text{Log}_{10}(L))^7 + I \cdot (\text{Log}_{10}(L))^8 \quad (6)$$

In equation (6), $\text{Log}_{10}$ represents a logarithm to the base 10, and the constants A-I may be set as follows: $A = 71.498068$, $B = 94.593053$, $C = 41.912053$, $D = 9.8247004$, $E = 0.28175407$, $F = -1.1878455$, $G = -0.18014349$, $H = 0.14710899$ and $I = -0.017046845$.

Equation (6) permits computing discrete INDs for the modality luminance range $(ML_{min}, ML_{max})$ as $j_{min} = j(ML^{min})$ and $j_{max} = j(ML_{max})$. In this regard, for a signed image, the span of j values may range from $j_{min}$ for pixel value $x = -2^{n-1}$, to $j_{max}$ for pixel value $x = 2^{n-1}-1$, such as according to the following:

$$j(x) = j_{min} + \frac{x + 2^{n-1}}{2^n - 1}(j_{max} - j_{min}) \quad (7)$$

For an unsigned image, the span of j values may range from $j_{min}$ for pixel value $x = 0$, to $j_{max}$ for pixel value $x = 2^{n-1}-1$, such as according to the following:

$$j(x) = j_{min} + \frac{x}{2^n - 1}(j_{max} - j_{min}) \quad (8)$$

The corresponding luminance values of each $j(x)$, then, can be calculated by equation (5) as $L(j(x))$.

In order to calculate the LUT, for each pixel value x calibrated according to the first calibration function, the corresponding LUT value may be found. This may be achieved by being given or otherwise determining the minimum and maximum luminance values ($ML_{min}$ and $ML_{max}$) and the gamma value ($\gamma$) of the monitor of the modality 12, which can be used to determine the parameters C and B of equation (4). Alternatively, in an instance in which the luminance range of the viewing station 14 monitor ($SL_{min}$ and $SL_{max}$) is known, and the gamma of the modality monitor is known, these values may be substituted in equation (4) to determine the parameters C and B. In another alternative, in an instance in which the parameters C and B and the gamma value of the modality monitor are given, these parameters may be used to determine the minimum and maximum luminance values ($ML_{min}$ and $ML_{max}$). In any instance, by substitution of $ML_{min}$ and $ML_{max}$ (or $SL_{min}$ and $SL_{max}$) in equation (6), one may determine the values of $j_{min}$ and $j_{max}$.

For each pixel value x, equation (4) may be used to determine G(x), which may be substituted into equation (6) to determine j(G(x)). The value j(G(x)) may be substituted into equation (7) or equation (8) (depending on the signed/unsigned nature of the image) to determine the value x as the corresponding LUT value. Written notationally, for a signed image, the LUT value may be determined from value j(G(x)) in accordance with the following:

$$LUT = \frac{j(G(x)) - j_{min}}{j_{max} - j_{min}}(2^n - 1) - 2^{n-1} \quad (9)$$

Or for an unsigned image, the LUT value may be determined from value j(G(x)) in accordance with the following:

$$LUT = \frac{j(G(x)) - j_{min}}{j_{max} - j_{min}}(2^n - 1) \quad (10)$$

As an example, consider the computing apparatus 16 being configured to transform pixel values calibrated according to gamma correction to corresponding pixel values calibrated according to DICOM GSDF. Further consider that the modality monitor (gamma calibrated) has the following parameter values: $ML_{min}=B=0.4$ cd/m$^2$, $ML_{max}=178$ cd/m$^2$, and $\gamma=2.2$. In this example, the LUT values for an 8-bit (n=8) unsigned image may be represented as in the graph of FIG. 4.

Alternatively, in an instance in which either or both of the first or second calibration functions are unknown, the LUT may be calculated by looking to the display characteristic curves of the modality 12 and viewing station 14, each of which may be determined or otherwise measured by means of a quantitative procedure. The display characteristic curve for a monitor may define the relationship between luminance and pixel values (equation (1) and (2) above). One may, for example, use TG18-LN test patterns for this purpose. These test patterns are provided by the American Association of Physicists in Medicine (AAPM), task group (TG) 18, and may be imported to the modality and sent to the viewing station to mimic an image workflow. By using test patterns such as the TG18-LN test patterns, a number of distinct luminance levels may be measured and the remaining luminance values may be interpolated, such as according to a cubic spline. The interpolated display characteristic curves of the modality and viewing station may then be used to determine the LUT, such as by taking equation (3) into consideration.

More particularly, for example, assume that the modality and viewing station transfer functions are measured and described by the following tabulated functions:

$$ML_i = G(x_i) \quad (11)$$

$$SL_j = F(x_j) \quad (12)$$

In equations (11) and (12), $x_i$ represents a pixel value calibrated according to the first calibration function, and $x_j$ represents a pixel value calibrated according to the second calibration function, each of which may be in the range $[-2^{n-1}, 2^{n-1}-1]$ for a signed image or $[0, 2^n-1]$ for an unsigned image. $ML^i$ represents the modality luminance for its pixel value $x_i$, and $SL_j$ represents the viewing station luminance for its pixel value $x_j$. The LUT may then be calculated according to the following pseudo-algorithm for a signed image:

For each integer i from range $[-2^{n-1}, 2^{n-1}-1]$ do
  For each integer j from range $[-2^{n-1}, 2^{n-1}-1]$ do
    Find a single $SL_j$ where $|ML_i - SL_j|$ has the minimum value
    Save $(x_i, x_j)$ A similar pseudo-algorithm may be implemented for an unsigned image by appropriately adjusting the range of i and j values. After execution of above algorithm, the LUT may be uniquely defined by the set of $(x_i, x_j)$ values.

Returning to FIG. 3, after calculating or otherwise retrieving the LUT, the method of an example embodiment may include receiving an image including a plurality of pixels each of which has a pixel value calibrated according to the first calibration function, as shown in block 42. The image may be formatted in any of a number of different manners, such as in accordance with the DICOM standard. The method may include applying the LUT to determine for each pixel value of each pixel of the image, a corresponding pixel value (LUT value) calibrated according to the second calibration function, as shown in block 44. The thus transformed pixel values may then be further processed, as appropriate, and output to the monitor of the viewing station 14 for display, as shown in block 46.

The LUT may be applied in any of a number of different manners, and at a number of different locations in an image workflow from a modality 12 to viewing station 14. In one example in which the second calibration function is the DICOM GSDF, the LUT may be applied as a presentation LUT or value-of-interest LUT in accordance with appropriate DICOM standards. Also, the LUT may be applied by the computing apparatus 16 which may be implemented as part of the imaging modality 12 or viewing station 14, or as a separate device between the modality and viewing station. The computing apparatus (separate or part of the modality) may be configured to add the LUT as a presentation LUT. The LUT values may be burned or otherwise stored with the respective pixels of the image, or the LUT may be passed through with the image. In another example in which the computing apparatus is implemented at the viewing station, image viewer software on the viewing station may be configurable to apply the LUT as a presentation LUT.

In various instances, particularly when the computing apparatus 16 is implemented separate from the imaging modality 12, the computing apparatus may be configured to apply different LUTs for different types of modalities (e.g., modalities 12a, 12b, 12c). In such instances, the computing apparatus may be configured to determine the type of modality that captured an image, and load and apply an appropriate LUT for the respective type of modality. The computing apparatus may be configured to determine the type of modality in a number of different manners.

In one example in which the imaging modalities 12 and computing apparatus 16 are coupled to and configured to communicate with one another across a network, each imaging modality may have a respective network address (e.g., IP address). In this example, the computing apparatus may store or otherwise have access to a table that associates the network addresses of the modalities with their modality types. When the computing apparatus receives an image across the network, the image or a record referring to the image may identify the network address of its source modality. The computing apparatus may then consult the table based upon the source network address to identify the type of the respective modality.

In another example, the image may be formatted to include a header with one or more tags including respective acquisition parameters that refer to the name of the modality 12 that acquired the image (source modality), its software version or the like. In this other example, the computing apparatus 16 may store or otherwise have access to a table that associates acquisition parameters (tags) with modality types, or may be setup to operate according to logic that specifies application of the LUT in instances in which an image has parameters (tags) with particular values. When the computing apparatus receives an image, the computing apparatus may be configured to analyze the image's header and its parameters (tags), and apply the LUT in accordance with the table or logic.

In a more particular example, a DICOM image may include a tag (0008, 0070) that identifies the "Manufacturer ID," tag (0008, 1090) that identifies the "Manufacturer's Model Name ID," tag (0008, 0060) that identifies the "Modality ID" and tag (0008, 1010) that includes a name identifying the machine that produce images. In this example, the computing apparatus 16 may be configured to apply the LUT in instances in which the computing apparatus receives an image from US (ultrasound) modality X with the name "koko" and software version "12.1.1." When the computing apparatus receives a DICOM image for display, the computing apparatus may be configured to analyze the image's header and its parameters. In an instance in which the "Modality ID" is US and "Manufacturer's Model Name ID" is "koko," the computing apparatus may apply the LUT; otherwise, the computing apparatus may forego application of the LUT.

To further illustrate example embodiments of the present invention, consider a hypothetical image workflow investigation in which the same image was displayed on an image-modality monitor with gamma calibration, and on a PACS viewing station with DICOM GSDF calibration. This investigation indicated that there would be no visual consistency in image display on monitors that were calibrated to gamma and DICOM GSDF calibration functions. As an example, FIG. 5 illustrates the derivatives of equations (4) and (5) for a luminance range of [0.36, 177] for a pixel range [0, 255]. Note that the vertical axis is the degree of luminance change (image contrast d(L)/d(x)), and it is in a logarithmic scale. The derivative of equation (5) (DICOM GSDF) is close to a linear line indicating perceptual linearity (the thick line in the figure), while the derivative of equation (4) (gamma calibration) is not a line but a logarithmic function in a logarithmic scale.

Even further, consider tests of a real-world workflow in which three ultrasound devices using gamma calibration, noted as USX, USY and USZ, sent images to a PACS viewing station connected to a monitor calibrated to DICOM GSDF. In these tests, patterns similar to TG18-LN were used, and the measured display characteristic curves of ultrasound devices and PACS monitor were determined (including cubic spline interpolation). The gamma values (γ) of the ultrasound device monitors were estimated by minimizing the mean square errors (MSE) of equation (4) and measured display characteristic values. The PACS monitor was a color LG 1200ME monitor with a resolution 280× 1024, and with a color temperature set to 6500 K. Its display characteristics curve was evaluated with the ideal DICOM GSDF function.

The above real-world workflow investigation provided the following results for the measured minimum and maximum luminance values, gamma values (γ) and MSEs:

| Device | Minimum L | Maximum L | Estimated γ | MSE |
|---|---|---|---|---|
| PACS | 0.36 | 177.52 | NA | 0.268 |
| USX | 0.18 | 153.08 | 2.27 | 0.261 |
| USY | 0.16 | 94.71 | 2.23 | 0.036 |
| USZ | 0.26 | 95.00 | 2.42 | 0.189 |

The deviation of the PACS monitor from the DICOM GSDF ideal curve was on average 5.5% with a minimum and maximum deviation of 0.5% and 12.3%, respectively. These measurements showed that the monitors were indeed calibrated according to the functions (gamma and DICOM GSDF), with the acceptable tolerance deviation from theoretical models.

The display characteristics of all four monitors in this example are shown in FIG. 6. As FIG. 6 illustrates, for smaller pixel values (<32), the PACS monitor produces more light. Usually pixel values of a smaller range are noise contribution to ultrasound images, and physicians often like noise to be displayed closer to pure black (minimum luminance). In addition, the derivatives of the display characteristics of the ultrasound devices and PCS monitor show a very similar discrepancy in image contrast as illustrated by the theoretical discrepancy shown in FIG. 5.

As noted above, some computing devices that display medical images are not dedicated to the display of medical images and, instead, may also be configured to display a variety of other types of images including, for example, images associated with video games, movies or other types of content. Even though these computing devices may not employ a DICOM GSDF calibration function in the manner described above in conjunction with other embodiments, the medical images are advantageously processed so as to appear consistent with the manner in which the medical images are displayed by other viewing stations, such as a PACS viewing station. However, the images generated by other applications executed by the computing device may appear unusual or inappropriate if transformed in the same manner as the medical images.

Thus, the computing device of an example embodiment may be configured to process certain types of images, such as medical images presented by an image viewing application, in one manner and to process other types of images presented by other applications in another manner. For example, the computing device may be configured to process medical images presented by an image viewing application so to appear as though the medical images have been visualized on a display that has been calibrated in accordance with DICOM GSDF (even though the computing device does not employ a DICOM GSDF calibration function), while the images that are presented by other applications are processed and displayed in accordance with a different calibration function, that is, a calibration function that is more suitable for these other, non-medical images.

The operations performed, such as by computing apparatus 16, in order to differently process the images presented by different types of applications are depicted in FIG. 7. As described above, the computing device 16 may be embodied by a computer workstation, a desktop computer, a personal computer, a server or a mobile device, such as a laptop computer, a tablet computer, a mobile telephone, a smartphone, a personal digital assistant (PDA) and the like. Although depicted in FIG. 2 as separate entities, the computing device 16 and the viewing station 14 may be co-located and, in an example embodiment, the display adapter 32 and the monitor 28 of the computing apparatus may constitute the viewing station.

As illustrated in block 50 in FIG. 7, the computing apparatus 16, such as the processor 20, may be configured to determine the application that is currently configured to drive the display, e.g., the monitor 28, such as by causing one or more images to be presented by the display. In this regard, a single application may be active and executing such that the single application is determined by the processor 20 to be capable of driving the display. Alternatively, multiple applications may be active and executing with the processor 20 being configured to determine that the application executing in the foreground is currently configured to drive the display instead of the other application(s) that are executing in the background. As shown in FIG. 7, the computing apparatus 16, such as the processor 20, may be configured to determine whether an image viewing application, such as may be utilized to review medical images, is currently configured to drive the display or if another, second application, such as a video game application, a word processing application, a movie player application, a mapping application or the like, is currently configured to drive the display.

As shown in block 54 of FIG. 7, in an instance in which an image viewing application is determined to be currently configured to drive the display, the computing apparatus 16, such as the processor 20, may be configured to identify the image calibration function associated with the image viewing application. For example, the imaging calibration function may be stored in memory 22 such that the processor 20 may identify the imaging calibration function by accessing memory to determine the calibration function associated with the image viewing application.

The imaging calibration function may be defined in various manners, such as described above in conjunction with FIG. 4. For example, the imaging calibration function may be defined based upon information provided by the manufacturer of the computing device 16. In this regard, the information provided by the manufacturer of the computing device may define the gamma value and the minimum and maximum luminance values from which the corresponding imaging calibration function may be defined. Alternatively, the imaging calibration function may be defined based upon luminance measurements of predefined phantom images, such as TG18-LN test patterns as described above. For example, 18 luminance measurements may be made of square panes of the display presenting pixel values in the range of 0 to 4095. Based upon the measurements and known ambient illuminance in the environment, such as in a typical work environment, a corresponding intensity calibration function may be defined.

In one example embodiment, the image viewing application may be configured to be executed by a plurality of different models of displays, such as a first tablet computer manufactured by a first company, a second tablet computer manufactured by a second company, etc. In this example embodiment, the imaging calibration function associated with the image viewing application may be defined for each type of display, such as each different model of display, upon which the image viewing application is configured to execute. In this embodiment, the computing apparatus 16, such as the processor 20, may be configured as shown in block 52 of FIG. 7 to determine the type of display, such as the model of the display, and to thereafter identify the imaging calibration function based upon the type of the display. The computing apparatus 16, such as the processor 20, may be configured to determine the type of display in various manners. In one example embodiment, the memory 22 may store information indicative of the type of display such that the processor 20 may be configured to access the memory to determine the type of display. Alternatively, the processor 20 may be configured to communicate with the display in order to obtain information that identifies the type of the display. In either instance, the processor 20 may then be configured to identify the appropriate imaging calibration function based upon the type of display.

As shown in block 56 of FIG. 7, in an instance in which the image viewing application is currently configured to drive the display and once the imaging calibration function has been identified, the computing apparatus 16, such as the processor 20, may be configured to transform a digital image, such as a medical image, during execution of the image viewing application. As described above, the digital image includes a plurality of pixels, each of which has a pixel value from among a plurality of pixel values, e.g., 0-255, 0-1023, 0-4095, etc. In this regard, the computing apparatus 16, such as the processor 20, may be configured at block 58 to transform the digital image by transforming the pixel value of at least some of the pixels to corresponding transformed pixel values calibrated according to the imaging calibration function. Thereafter, the computing apparatus 16, such as the processor 20, may be configured to cause output of the digital image in accordance with the image viewing application. In this regard, the digital image that is output includes the plurality of pixels of which at least some have a transformed pixel value.

By transforming the digital image in accordance with the imaging calibration function, the resulting digital image that is presented by the display may appear in a manner consistent with that expected by a user. In regards to a medical image, for example, the digital image may be transformed in accordance with the imaging calibration function such that the resulting digital image presented by the display appears as though the digital image has been displayed on a monitor, which has been calibrated in accordance with the DICOM GSDF even though the computing device is not configured to calibrate an image in accordance with DICOM GSDF. Consequently, a user may more efficiently and accurately read and interpret the image, such as a medical image, as a result of the transformation of the digital image according to the imaging calibration function.

As noted above, as the computing device 16 need not necessarily be dedicated to the presentation of medical images, the computing device may be configured to present other types of images that may be more appropriately processed in accordance with a different calibration function so as to have the desired appearance and effect. As such, in an instance in which the computing apparatus 16, such as the processor 20, determines that an application, herein referenced as a second application, other than the image viewing application is currently configured to drive the display, the computing apparatus, such as the processor, is configured to identify the second calibration function associated with the second application as shown in block 64 of FIG. 7. In this regard, the second calibration function may be identified in various manners. In one example embodiment, the second calibration function may be stored by memory 22 such that the processor 20 may identify the second calibration function by reference to the memory. Although not depicted in FIG. 7, the determination of the second calibration function may also be based upon the type of display, such as described above in conjunction with block 52 of FIG. 7.

Once the second calibration function has been identified, the computing apparatus 16, such as the processor 20, may be configured at block 66 to transform a digital image during execution of the second application by transforming the pixel values of at least some of the pixels of the digital image to corresponding transformed pixel values processed according to the second calibration function. Thereafter, the computing apparatus 16, such as the processor 20, may be configured at block 68 to cause output of the digital image in accordance with the second application. In this regard, the digital image that is output includes a plurality of pixels of which at least some have been transformed in accordance with the second calibration function. By processing at least some of the pixels of the digital image in accordance with the second calibration function, the resulting digital image may be more appropriate for a user viewing the output of the second application, even though the digital image is transformed in a different manner than that in which a medical image presented in accordance with the image viewing application would have been transformed.

The calibration functions may be defined in various manners. As described above, the calibration functions may be defined by respective lookup tables that associate pixel values of the original digital image, such as the digital image captured by a modality and processed in accordance with a modality calibration function in the context of a medical image, to corresponding pixel values that will cause the display to provide the desired luminance. As such, a first lookup table may be defined by and associated with the imaging calibration function and a second lookup table, different than the first lookup table, may be defined by and associated with the second calibration function. In an example embodiment, each of the lookup tables may be stored by memory 22.

Once the transformed digital image has been output by the display, the computing apparatus 16, such as the processor 22, may be configured to determine whether the respective application, such as the image viewing application or the second application, is continuing to drive the display, such as shown in block 60 in conjunction with the image viewing application and in block 70 in conjunction with the second application. In an instance in which the respective application is no longer driving the display, such as an instance in which the respective application has been closed or moved to the background, the computing apparatus 16, such as the processor 20, may be configured to repeat the process by again determining the application that is currently configured to drive the display as shown in block 50 of FIG. 7 and as described above. However, in an instance in which the respective application continues to drive the display, the computing apparatus 16, such as the processor 20, may be configured to determine whether another digital image is to be displayed in shown in blocks 62 and 72 of FIG. 7. In an instance in which another digital image is not currently slated to be displayed, the computing apparatus 16, such as the processor 20, may be configured to repeatedly determine whether the respective application continues to drive the display and, if so, if another digital image is ready to be displayed. However, in an instance in which the computing apparatus 16, such as the processor 20, does determine that another digital image is to be displayed, the computing apparatus, such as the processor, may be configured to repeat the process of transforming the digital image in accordance with the respective calibration function and to thereafter cause output of the transformed digital image in accordance with the respective application as shown in FIG. 7 and as described above.

In another example embodiment, the calibration function that is identified may be set as the active calibration function with the digital image subsequently transformed in accordance with the active calibration function and the digital image thereafter output following transformation by the active calibration function in accordance with the respective application that is currently configured to drive the display. In accordance with this example embodiment and as shown in FIG. 8, the computing apparatus 16, such as the processor 20, may be configured to determine the application that is currently configured to drive the display and to thereafter identify the calibration function, such as the imaging calibration function or the second calibration function, based upon the application that was determined to be currently configured to drive the display. See blocks 80, 84 and 96 of FIG. 8. As described above, the determination of the calibration function may also be based upon the type of display. See block 82 of FIG. 8.

In an instance in which the image viewing application is currently configured to drive the display and an imaging calibration function has been correspondingly identified, the computing apparatus 16, such as the processor 20, may be configured to set the imaging calibration function as the active calibration function. See block 86 of FIG. 8. Alternatively, in an instance in which the second application is determined to currently be configured to drive the display and the second calibration function has been correspondingly identified, the computing apparatus 16, such as the processor 20, may be configured to set the second calibration function as the active calibration function. See block 98 of FIG. 8.

Thereafter, the computing apparatus 16, such as the processor 20, may be configured to transform the digital image in accordance with the active calibration function and to cause the output of the digital image, following its transformation, in accordance with the respective application that was determined to currently be configured to drive the display. See blocks 88 and 90 of FIG. 8. As shown in blocks 92 and 94 of FIG. 8, the computing apparatus 16, such as the processor 20, may thereafter be configured to determine whether the same application is continuing to be configured to drive the display and, if so, whether another digital image is slated to be displayed. If so, the computing apparatus 16, such as the processor 20, may be configured to repeat the process of transforming the digital image in accordance with the active calibration function and to cause output of the digital image, following its transformation, in accordance with the respective application. Alternatively, in an instance in which the computing apparatus 16, such as the processor 20, determines that the same application is no longer configured to drive the display, the computing apparatus, such as the processor, may be configured to repeat the overall process by again determining the application that is currently configured to drive the display, as shown in block 80 of FIG. 8. Still further, in an instance in which the computing apparatus 16, such as the processor 20, determines that another digital image is not currently slated to be displayed, the computing apparatus, such as the processor, may repeat the process depicted in blocks 92 and 94 of determining whether the same application is currently configured to drive the display and, if so, whether or not a digital image is ready to be displayed.

In an example embodiment, the computing apparatus 16, such as the processor 20, may be configured to maintain the second calibration function as the active calibration function by default, such as in all instances other than those in which the image viewing application is determined to be currently configured to drive the display. In this embodiment, the imaging calibration function may be set as the active calibration function in an instance in which the image viewing application is determined to be currently configured to drive the display. However, once the computing apparatus 16, such as the processor 20, determines that the image viewing application is no longer configured to drive the display, such as in response to deactivation of or exiting out of the image viewing application, the computing apparatus, such as the processor, may be configured to reset the second calibration function to be the active calibration function, at least until such time that the image viewing application is again determined to be currently configured to drive the display.

As described, example embodiments of the present invention provide an apparatus, method and computer-readable storage medium for processing images, such as medical images, such that the image that is presented has an appearance with which the user is familiar and which may therefore be more readily read and interpreted. For example, the apparatus, method and computer-readable storage medium of an example embodiment may transform images in a manner that causes images to be presented that appear to have been displayed by a monitor that has been calibrated in accordance with DICOM GSDF even though the computing apparatus 16 and/or the viewing station 14 is not configured to provide for DICOM GSDF calibration. Additionally, the apparatus, method and computer-readable storage medium of an example embodiment may permit processing in accordance with an imaging calibration function during execution of an image viewing application, but in accordance with a different calibration function, that is, a second calibration function, during execution of a different application, thereby supporting the presentation of images by computing devices that are not dedicated to viewing medical images.

According to one aspect of the present invention, all or a portion of the modality 12, viewing station 14 and/or computing apparatus 16 of an example embodiment of the present invention, generally operate under control of a computer program. The computer program for performing the methods of an example embodiment of the present invention may include one or more computer-readable program code portions, such as a series of computer instructions, embodied or otherwise stored in a computer-readable storage medium, such as the non-volatile storage medium.

FIGS. 3, 7 and 8 are flowcharts reflecting methods, systems and computer programs according to example embodiments of the present invention. It will be understood that each block or step of the flowcharts, and combinations of blocks in the flowcharts, may be implemented by various means, such as hardware, firmware, and/or software including one or more computer program instructions. As will be appreciated, any such computer program instructions may be loaded onto a computer or other programmable apparatus to produce a machine, such that the instructions which execute on the computer or other programmable apparatus (e.g., hardware) create means for implementing the functions specified in the block(s) or step(s) of the flowcharts. These computer program instructions may also be stored in a computer-readable memory that may direct a computer or other programmable apparatus to function in a particular manner, such that the instructions stored in the computer-readable memory produce an article of manufacture including instruction means which implement the function specified in the block(s) or step(s) of the flowcharts. The computer program instructions may also be loaded onto a computer or other programmable apparatus to cause a series of operational steps to be performed on the computer or other programmable apparatus to produce a computer-implemented process such that the instructions which execute on the computer or other programmable apparatus provide steps for implementing the functions specified in the block(s) or step(s) of the flowcharts.

Accordingly, blocks or steps of the flowcharts support combinations of means for performing the specified functions, combinations of steps for performing the specified functions and program instruction means for performing the specified functions. It will also be understood that one or more blocks or steps of the flowcharts, and combinations of blocks or steps in the flowcharts, may be implemented by special purpose hardware-based computer systems which perform the specified functions or steps, or combinations of special purpose hardware and computer instructions.

In some embodiments, certain ones of the operations herein may be modified or further amplified as described below. Moreover, in some embodiments additional optional operations may also be included, such as indicated by the dashed blocks 52 and 82 in FIGS. 7 and 8, respectively. It should be appreciated that each of the modifications, optional additions or amplifications below may be included with the operations above either alone or in combination with any others among the features described herein.

The above described functions may be carried out in many ways. For example, any suitable means for carrying out each of the functions described above may be employed to carry out embodiments of the invention. In one embodiment, a suitably configured processor 20 may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. An apparatus comprising a processor and a memory storing executable instructions that in response to execution by the processor cause the apparatus to at least:
   determine whether a display is to be driven by an image viewing application or a second application, wherein the second application is different than the image viewing application and is configured to display an image other than a medical image, wherein the display is configured to be alternately driven by the image viewing application and the second application;
   in an instance in which the image viewing application is configured to drive the display:
   identify an imaging calibration function;
   transform, during execution of the image viewing application, a digital image that includes a plurality of pixels, each of which has a pixel value from among a plurality of pixel values, wherein the digital image is transformed by transforming the pixel value of at least some of the pixels to corresponding transformed pixel values processed according to the imaging calibration function, wherein the apparatus being caused to transform the digital image during execution of the image viewing application includes being caused to transform the pixel value of at least some of the pixels according to a lookup table associated with the imaging calibration function; and
   cause output of the digital image in accordance with the image viewing application, wherein the digital image that is output comprises a medical image and includes the plurality of pixels of which at least some have a transformed pixel value; and
   in an instance in which the second application, different than the image viewing application, is configured to drive the display:
   identify a second calibration function, different than the imaging calibration function;
   transform, during execution of the second application, a digital image by transforming the pixel value of at least some of the pixels to corresponding transformed pixel values processed according to the second calibration function; and cause output of the digital image in accordance with the second application, wherein the digital image that is output is an image other than a medical image and includes a plurality of pixels of which at least some have been transformed in accordance with the second calibration function, wherein the output of the digital image that is presented by the display includes pixels that have been transformed in accordance with a different calibration function depending upon whether the image viewing application or the second application is configured to drive the display.

2. The apparatus of claim 1, wherein the apparatus being caused to transform the digital image during execution of the second application includes being caused to transform the pixel value of at least some of the pixels according to a lookup table associated with the second calibration function, wherein the lookup table associated with the second calibration function is different than the lookup table associated with the imaging calibration function.

3. The apparatus of claim 1, wherein the apparatus being caused to output the digital image in accordance with the image viewing application includes being caused to present the digital image upon a display, wherein the imaging calibration function is dependent upon a type of the display, wherein the memory stores executable instructions that in response to execution by the processor further cause the apparatus to determine the type of display upon which the digital image is to be presented, and wherein the apparatus being caused to identify the imaging calibration function includes being caused to identify the imaging calibration function based upon the type of display.

4. The apparatus of claim 3, wherein the memory is configured to store a plurality of imaging calibration functions with each imaging calibration function associated with a respective type of display.

5. The apparatus of claim 1, wherein the memory stores executable instructions that in response to execution by the processor further cause the apparatus to set the imaging calibration function as an active calibration function upon actuation of the image viewing application and identification of the imaging calibration function and to reset the second calibration function as the active calibration function once the image viewing application is exited, wherein the apparatus being caused to transform the digital image includes being caused to transform the digital image in accordance with the active calibration function.

6. A method comprising:
determining whether a display is to be driven by an image viewing application or a second application, wherein the second application is different than the image viewing application and is configured to display an image other than a medical image, wherein the display is configured to be alternately driven by the image viewing application and the second application;
in an instance in which the image viewing application is configured to drive the display: identifying an imaging calibration function;
transforming, with a processor, a digital image during execution of the image viewing application, wherein the digital image includes a plurality of pixels, each of which has a pixel value from among a plurality of pixel values, and wherein the digital image is transformed by transforming the pixel value of at least some of the pixels to corresponding transformed pixel values processed according to the imaging calibration function, wherein transforming the digital image during execution of the image viewing application includes transforming the pixel value of at least some of the pixels according to a lookup table associated with the imaging calibration function; and
causing output of the digital image in accordance with the image viewing application, wherein the digital image that is output comprises a medical image and includes the plurality of pixels of which at least some have a transformed pixel value; and
in an instance in which the second application, different than the image viewing application is configured to drive the display:
identifying a second calibration function, different than the imaging calibration function;
transforming, during execution of the second application, a digital image by transforming the pixel value of at least some of the pixels to corresponding transformed pixel values processed according to the second calibration function; and
causing output of the digital image in accordance with the second application, wherein the digital image that is output is an image other than a medical image and includes a plurality of pixels of which at least some have been transformed in accordance with the second calibration function,
wherein the output of the digital image that is presented by the display includes pixels that have been transformed in accordance with a different calibration function depending upon whether the image viewing application or the second application is configured to drive the display.

7. The method of claim 6, wherein transforming the digital image during execution of the second application includes transforming the pixel value of at least some of the pixels according to a lookup table associated with the second calibration function, wherein the lookup table associated with the second calibration function is different than the lookup table associated with the imaging calibration function.

8. The method of claim 6, wherein causing output of the digital image in accordance with the image viewing application includes causing presentation of the digital image upon a display, wherein the imaging calibration function is dependent upon a type of the display, wherein the method further comprises determining the type of display upon which the digital image is to be presented, and wherein identifying the imaging calibration function includes identifying the imaging calibration function based upon the type of display.

9. The method of claim 8, further comprising storing a plurality of imaging calibration functions with each imaging calibration function associated with a respective type of display.

10. The method of claim 6, further comprising:
setting the imaging calibration function as an active calibration function upon actuation of the image viewing application and identification of the imaging calibration function; and
resetting the second calibration function as the active calibration function once the image viewing application is exited,
wherein transforming the digital image includes transforming the digital image in accordance with the active calibration function.

11. A non-transitory computer-readable storage medium having computer-readable program code portions stored therein that, in response to execution by a processor, cause an apparatus at least to:
    determine whether a display is to be driven by an image viewing application or a second application, wherein the second application is different than the image viewing application and is configured to display an image other than a medical image, wherein the display is configured to be alternately driven by the image viewing application and the second application;
    in an instance in which the image viewing application is configured to drive the display:
    identify an imaging calibration function;
    transform a digital image during execution of the image viewing application, wherein the digital image includes a plurality of pixels, each of which has a pixel value from among a plurality of pixel values, and wherein the digital image is transformed by transforming the pixel value of at least some of the pixels to corresponding transformed pixel values processed according to the imaging calibration function, wherein the apparatus being caused to transform the digital image during execution of the image viewing application includes being caused to transform the pixel value of at least some of the pixels according to a lookup table associated with the imaging calibration function; and
    cause output of the digital image in accordance with the image viewing application, wherein the digital image that is output comprises a medical image and includes the plurality of pixels of which at least some have a transformed pixel value; and
    an instance in which the second application, different than the image viewing application is configured to drive the display:
    identify a second calibration function, different than the imaging calibration function;
    transform, during execution of the second application, a digital image by transforming the pixel value of at least some of the pixels to corresponding transformed pixel values processed according to the second calibration function; and
    cause output of the digital image in accordance with the second application, wherein the digital image that is output is an image other than a medical image and includes a plurality of pixels of which at least some have been transformed in accordance with the second calibration function,
    wherein the output of the digital image that is presented by the display includes pixels that have been transformed in accordance with a different calibration function depending upon whether the image viewing application or the second application is configured to drive the display.

12. The computer-readable storage medium of claim 11, wherein the apparatus being caused to transform the digital image during execution of the second application includes being caused to transform the pixel value of at least some of the pixels according to a lookup table associated with the second calibration function, wherein the lookup table associated with the second calibration function is different than the lookup table associated with the imaging calibration function.

13. The computer-readable storage medium of claim 11, wherein the apparatus being caused to output the digital image in accordance with the image viewing application includes being caused to present the digital image upon a display, wherein the imaging calibration function is dependent upon a type of the display, wherein the computer-readable program code portions further cause the apparatus to determine the type of display upon which the digital image is to be presented, and wherein the apparatus being caused to identify the imaging calibration function includes being caused to identify the imaging calibration function based upon the type of display.

14. The computer-readable storage medium of claim 11, wherein the computer-readable program code portions further cause the apparatus to set the imaging calibration function as an active calibration function upon actuation of the image viewing application and identification of the imaging calibration function and to reset the second calibration function as the active calibration function once the image viewing application is exited, wherein the apparatus being caused to transform the digital image includes being caused to transform the digital image in accordance with the active calibration function.

15. The apparatus of claim 1, wherein the apparatus is caused to determine whether the display is to be driven by the image viewing application or the second application based on whether the image viewing application or the second application is executing in a foreground, wherein an application executing in the foreground is determined to be driving the display while an application executing in a background is determined to not be driving the display.

16. The method of claim 6, wherein determining whether the display is to be driven by the image viewing application or the second application is based on whether the image viewing application or the second application is executing in a foreground, wherein an application executing in the foreground is determined to be driving the display while an application executing in a background is determined to not be driving the display.

17. The computer-readable storage of claim 11, wherein the apparatus is caused to determine whether the display is to be driven by the image viewing application or the second application based on whether the image viewing application or the second application is executing in a foreground, wherein an application executing in the foreground is determined to be driving the display while an application executing in a background is determined to not be driving the display.

18. The apparatus of claim 1, wherein the second application comprises a video game application, a word processing application, a movie player application or a mapping application.

19. The method of claim 6, wherein the second application comprises a video game application, a word processing application, a movie player application or a mapping application.

20. The computer-readable storage of claim 11, wherein the second application comprises a video game application, a word processing application, a movie player application or a mapping application.

* * * * *